United States Patent
Stadler

(10) Patent No.: US 11,376,418 B2
(45) Date of Patent: Jul. 5, 2022

(54) METHOD OF ESTIMATING HEART RATE AND DETECTING TACHYARRHYTHMIA

(71) Applicant: Medtronic, Inc., Minneapolis, MN (US)

(72) Inventor: Robert W. Stadler, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 47 days.

(21) Appl. No.: 16/680,758

(22) Filed: Nov. 12, 2019

(65) Prior Publication Data

US 2020/0155742 A1    May 21, 2020

Related U.S. Application Data

(60) Provisional application No. 62/767,779, filed on Nov. 15, 2018.

(51) Int. Cl.
*A61N 1/39* (2006.01)
*A61M 60/50* (2021.01)
*A61M 60/148* (2021.01)

(52) U.S. Cl.
CPC .......... *A61M 60/50* (2021.01); *A61M 60/148* (2021.01); *A61M 2205/18* (2013.01); *A61M 2205/3553* (2013.01); *A61M 2230/04* (2013.01)

(58) Field of Classification Search
CPC ......... A61B 5/363; A61B 5/029; A61B 5/053; A61B 5/352; A61B 5/6869; A61N 1/37;
(Continued)

(56) References Cited

U.S. PATENT DOCUMENTS 7,645,225 B2   1/2010   Medvedev et al.
7,765,002 B2   7/2010   Ettori et al.
(Continued)

FOREIGN PATENT DOCUMENTS

EP   2585129 B1   3/2017
WO   0057779 A1   10/2000
(Continued)

OTHER PUBLICATIONS

International Search Report and Written Opinion dated Apr. 9, 2020, for corresponding International Application No. PCT/US2019/060829; International Filing Date: Nov. 12, 2019 consisting of 11—pages.
(Continued)

*Primary Examiner* — Jon Eric C Morales
(74) *Attorney, Agent, or Firm* — Shumaker & Sieffert, P.A.

(57) ABSTRACT

A method of estimating a heart rate of a patient having an implantable blood pump including, during operation of the blood pump continuously detecting a plurality of cardiac cycles, each of the plurality of cardiac cycles including a length; sorting the plurality of cardiac cycles according to the length; filtering the plurality of cardiac cycles between one of a group consisting of including a reliable condition and at least one unreliable condition; continuously estimating a heart rate according to the length of the plurality of cardiac cycles and the reliable condition; and if the at least one unreliable condition is detected, modifying the estimated heart rate based on information associated with the detected at least one unreliable condition.

9 Claims, 13 Drawing Sheets

(58) Field of Classification Search
CPC .. A61N 1/3925; A61N 1/3622; A61N 1/3621; A61N 1/36842; A61N 1/36843; A61N 1/398

See application file for complete search history.

(56) References Cited

U.S. PATENT DOCUMENTS

| | | | |
|---|---|---|---|
| 7,787,946 | B2 | 8/2010 | Stahmann et al. |
| 7,890,170 | B2 | 2/2011 | Ettori et al. |
| 8,437,849 | B2 | 5/2013 | Kim et al. |
| 9,554,717 | B2 | 1/2017 | Keel et al. |
| 10,159,775 | B2 | 12/2018 | Voskoboynikov et al. |
| 2007/0282298 | A1 | 12/2007 | Mason |
| 2011/0196247 | A1 | 8/2011 | Cao et al. |
| 2011/0270109 | A1 | 11/2011 | Zhang et al. |
| 2011/0270333 | A1 | 11/2011 | Stadler et al. |
| 2016/0101230 | A1* | 4/2016 | Ochsner ............... A61B 5/1073 600/17 |
| 2016/0106991 | A1 | 4/2016 | Stadler et al. |
| 2017/0312520 | A9 | 11/2017 | Zhang et al. |
| 2018/0028737 | A1 | 2/2018 | Reyes et al. |
| 2018/0085506 | A1 | 3/2018 | Yomtov et al. |

FOREIGN PATENT DOCUMENTS

| | | |
|---|---|---|
| WO | 2012154489 A1 | 11/2012 |
| WO | 2018026655 A2 | 2/2018 |
| WO | 2018165289 A1 | 9/2018 |

OTHER PUBLICATIONS

International Preliminary Report on Patentability from International Application No. PCT/US2019/060829, dated May 18, 2021, 8 pp.

Moscato et al., "Continuous Monitoring of Cardiac Rhythms in Left Ventricular Assist Device Patients," Artificial Organs, vol. 38, Issue 3, pp. 191-198, Aug. 1, 2013.

* cited by examiner

| 1 | 2 | 3 | 4 | 5 | 6 | 7 | 8 | 9 | 10 | 11 | 12 |
|---|---|---|---|---|---|---|---|---|---|---|---|
| CC1 | CC2 | CC3 | CC4 | CC5 | CC6 | CC7 | CC8 | CC9 | CC10 | CC11 | CC12 |
| 410 | 420 | 830 | 850 | 1680 | 1660 | 840 | 820 | 860 | 440 | 430 | 870 |

OS (cols 1–2), US (col 5), US (col 6), OS (cols 10–11), B (col 12)

FIG. 5

| 1 | 2 | 3 | 4 | 5 | 6 | 7 | 8 | 9 | 10 | 11 | 12 |
|---|---|---|---|---|---|---|---|---|---|---|---|
| CC1 | CC2 | CC11 | CC10 | CC8 | CC3 | CC7 | CC4 | CC9 | CC12 | CC6 | CC5 |
| 410 | 420 | 430 | 440 | 820 | 830 | 840 | 850 | 860 | 870 | 1660 | 1680 |

OS (col 1), OS (cols 2–4), US (col 6), US (col 11), US (col 12), B (col 12)

HR = 60000/830 = 72.3 BPM

FIG. 6

METHOD OF ESTIMATING HEART RATE AND DETECTING TACHYARRHYTHMIA

CROSS-REFERENCE TO RELATED APPLICATION

This application claims the benefit of U.S. Application Ser. No. 62/767,779, filed Nov. 15, 2018.

FIELD

The present technology is generally related to implantable blood pumps.

BACKGROUND

Mechanical circulatory support devices, such as implantable blood pumps, are used to assist the pumping action of a failing heart. Such blood pumps may include a housing with an inlet, an outlet, and a rotor mounted within the housing. The inlet may be connected to a chamber of a patient's heart, for example the left ventricle, using an inflow cannula. The outlet may be connected to an artery, such as the aorta. Rotation of the rotor drives blood from the inlet towards the outlet and thus assists blood flow from the chamber of the heart into the artery.

Known blood pumps are susceptible to experiencing adverse events which may result in costly hospitalizations and medical interventions for patients. For example, whether systemic or cardio-pulmonary in nature, adverse events can impact ventricular volume and pressure which is reflected in pump parameters such as power, flow, current, speed, and/or derivatives of pump parameters, such as a patient's circadian cycle, heart rate, aortic valve status, and suction burden. The pump parameters are controlled by a controller, such as through closed-loop pump control which operates based on feedback representing physiological demand. For example, pump speed may be controlled based on the patient's heart rate. When physiological demand is represented via waveforms, the waveforms are reviewed manually by a physician who estimates the patient's heart rate. Existing methods of controlling the pump speed relative to the heart rate do not automatically distinguish between reliable and unreliable heart rates, such as when the patient's pulsatility is relatively low.

SUMMARY

The techniques of this disclosure generally relate to estimating a heart rate of a patient having an implantable blood pump, during operation of the blood pump, using conditions considered to be reliable, while excluding conditions considered to be unreliable, as explained in further detail below.

In one aspect, the present disclosure provides a method of estimating a heart rate of a patient having an implantable blood pump including, during operation of the blood pump, continuously detecting one or more cardiac cycles, each of the cardiac cycles including a length; sorting the plurality of cardiac cycles according to the length; filtering the cardiac cycles between one of a group consisting of including a reliable condition and at least one unreliable condition; continuously estimating a heart rate according to the length of the cardiac cycles and the reliable condition; and if the at least one unreliable condition is detected, modifying the estimated heart rate based on information associated with the detected at least one unreliable condition.

In another aspect of this embodiment, at least one unreliable condition includes an individual heart rate estimate.

In another aspect of this embodiment, the unreliable condition is one of a group consisting of a low pulsatility, the plurality of cardiac cycles including a length deviating from a standard length, and a tachyarrhythmia.

In another aspect of this embodiment, the method further includes generating a low pulsatility alert when the unreliable condition is the low pulsatility, and, during a duration of the low pulsatility alert, automatically excluding the plurality of cardiac cycles from the heart rate estimating.

In another aspect of this embodiment, the plurality of cardiac cycles define a buffer, and the buffer is reset when the duration of the low pulsatility alert continues for a predetermined duration.

In another aspect of this embodiment, the method further includes defining a running average of a beat-to-beat difference in a pair of adjacent cardiac cycles of the plurality of cardiac cycles and classifying at least one of the plurality of cardiac cycles as including the unreliable condition when the running average is greater than a predetermined percentage of a predetermined average.

In another aspect of this embodiment, the method further includes detecting and maintaining an R-R expected range.

In another aspect of this embodiment, the plurality of cardiac cycles define a buffer, and the buffer is continuously maintained using a most recent plurality of cardiac cycles.

In another aspect, the disclosure provides a method of controlling an implantable blood pump including, during operation of the blood pump, detecting one or more cardiac cycles defining cardiac cycle data; designating the cardiac cycle data as including one of a group consisting of reliable information and an unreliable condition; in a presence of the reliable condition, continuously determining a heart rate using the cardiac cycle data, correlating the determined heart rate to a physiological demand, and controlling the blood pump using a closed-loop control system based on the determined physiological demand; and in a presence of the unreliable condition, using a secondary source of information different than the cardiac cycle data to determine the physiological demand, and control the blood pump according to the secondary source of information.

In another aspect of this embodiment, the method further includes altering a pump parameter based on the unreliable condition.

In another aspect of this embodiment, the unreliable condition includes an individual heart rate estimate.

In another aspect of this embodiment, the unreliable condition includes one of a group consisting of a low pulsatility, the plurality of cardiac cycles including a length deviating from a standard length, and a tachyarrhythmia.

In another aspect of this embodiment, the method further includes generating a low pulsatility alert when the unreliable condition is the low pulsatility and controlling the blood pump based on the secondary source of information during a duration of the low pulsatility alert.

In another aspect of this embodiment, the plurality of cardiac cycles define a buffer, and the buffer is continuously updated using the length of each of the plurality of cardiac cycles in real time.

In another aspect of this embodiment, the method further includes resetting the buffer when a duration of the low pulsatility alert continues for a predetermined duration.

In another aspect of this embodiment, the method further includes detecting a tachyarrhythmia and controlling the blood pump based on the secondary source of information during a duration of the tachyarrhythmia.

In another aspect of this embodiment, the method further includes generating an alert associated with the unreliable condition.

In another aspect, the disclosure provides a method of detecting a tachyarrhythmia in a patient having an implantable blood pump including, during operation of the blood pump, detecting the tachyarrhythmia; storing information associated with the tachyarrhythmia including a plurality of waveforms; and based on the tachyarrhythmia, performing a diagnostic function.

In another aspect of this embodiment, the plurality of waveforms includes at least one waveform before, during, and after the tachyarrhythmia.

In another aspect of this embodiment, the diagnostic function includes generating an alert, and transmitting the alert to a location remote from the blood pump.

In another aspect of this embodiment, the method further includes altering a pump parameter based on the tachyarrhythmia.

In another aspect, the disclosure provides a system of estimating a heart rate of a patient having an implantable blood pump including a controller including a processor, the processor being configured to, during operation of the blood pump, continuously detect one or more cardiac cycles, each of the cardiac cycles including a length; sort the cardiac cycles according to the length; filter the cardiac cycles between one of a group consisting of including a reliable condition and at least one unreliable condition; continuously estimate a heart rate according to the length of the cardiac cycles and the reliable condition; and if the at least one unreliable condition is detected, modify the estimated heart rate based on information associated with the detected at least one unreliable condition.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 5 is a table listing one or more cardiac cycles detected in accordance with the method of FIG. 2 and defining a buffer;

FIG. 6 is a table of the buffer of the cardiac cycles of FIG. 5 sorted from a smallest to a largest length;

DETAILED DESCRIPTION

Figure 1:
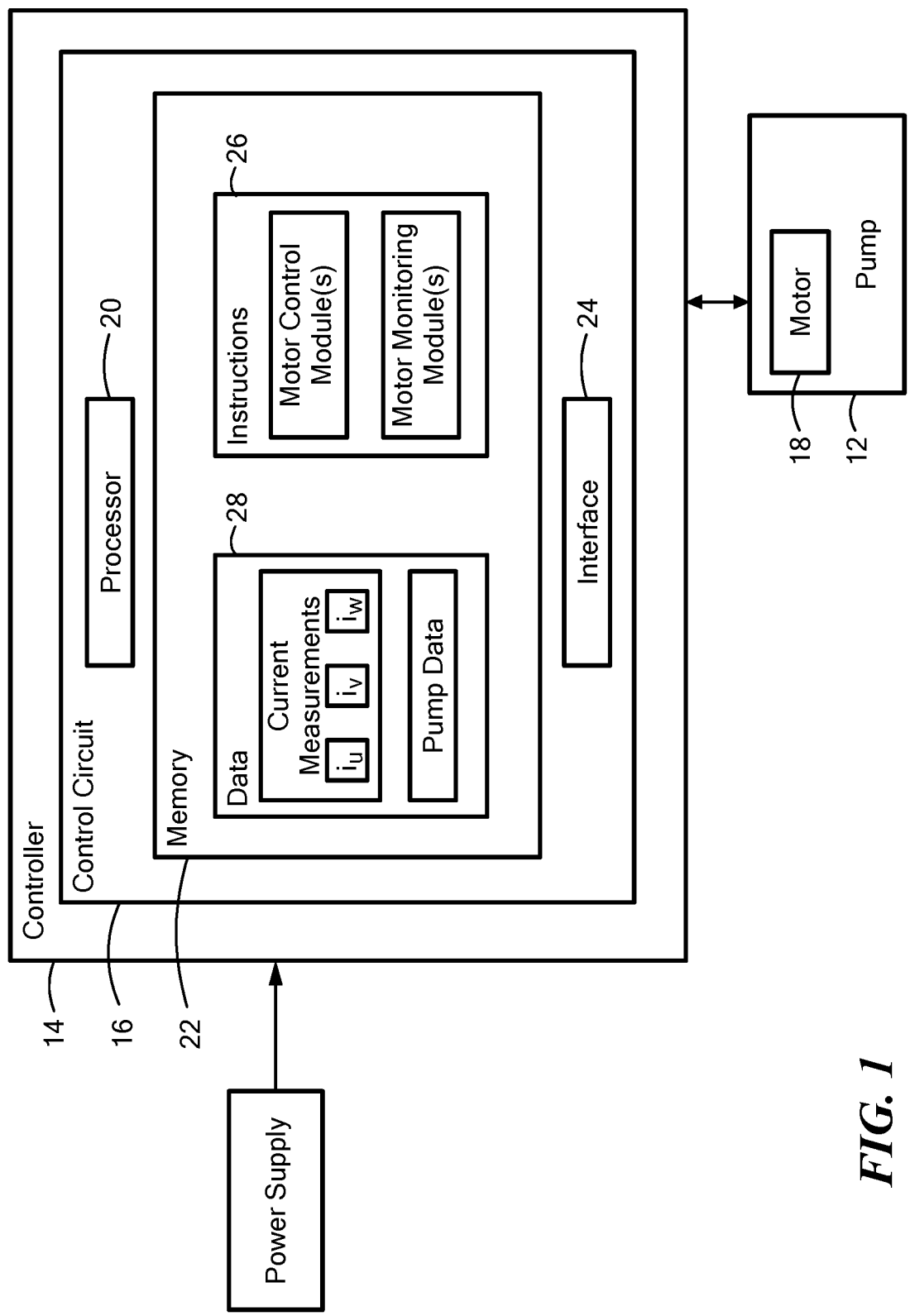
FIG. 1 is a block diagram that illustrates a system including an implantable blood pump and a controller including a processor in communication with the blood pump.

Before describing in detail exemplary embodiments, it is noted that the embodiments reside primarily in combinations of device, system components, and processing steps related to determining a heart rate of a patient with an implantable blood pump. Accordingly, the device, system, and process components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

Referring now to the drawings in which like reference designators refer to like elements, there is shown an exemplary system constructed in accordance with the principles of the present disclosure and designated generally as "10." The system, and corresponding methods, are configured to obtain physiologic information indicative of cardiac activity, including heart rate and pulsatility, and determine whether the physiologic information includes a reliable and/or an unreliable condition. The physiologic information may be determined through the blood pump's waveforms or another source of information. The reliable condition is used to estimate the patient's heart rate, whereas periods which include the unreliable condition are excluded from the heart rate estimate. The unreliable conditions are conditions which do not accurately reflect a patient's heart rate and physiologic demand and include, for example, low pulsatility, periods of highly variable cardiac cycles, such as bigeminy or atrial fibrillation, i.e., cardiac cycles which vary with respect to a number of other cardiac cycles, tachyarrhythmia, and/or individual cardiac cycle estimates. The determination as to whether the individual heart rate estimates are considered to be unreliable may be determined using information from the patient's cardiac cycles. The presence of the unreliable conditions may trigger an alert and/or alteration of a pump parameter. Further, the unreliable conditions may inhibit closed-loop control method such that the pump is controlled using physiological information from a secondary source of physiological information. Moreover, the system and method may be configured to detect a tachyarrhythmia for diagnostic purposes.

FIG. 1 is a block diagram of the system 10 including an implantable blood pump 12 in communication with a controller 14. The blood pump 12 may be the HVAD® Pump or another mechanical circulatory support device fully or partially implanted within the patient and having a movable element, such as a rotor, configured to pump blood from the heart to the rest of the body. The controller 14 includes a control circuit 16 for monitoring and controlling startup and subsequent operation of a motor 18 implanted within the blood pump 12. The controller 14 may also include a processor 20, a memory 22, and an interface 24 with the memory 22 being configured to store information accessible by the processor 20, including instructions 26 executable by the processor 20 and/or data 28 that may be retrieved, manipulated, and/or stored by the processor 20.

Figure 2:
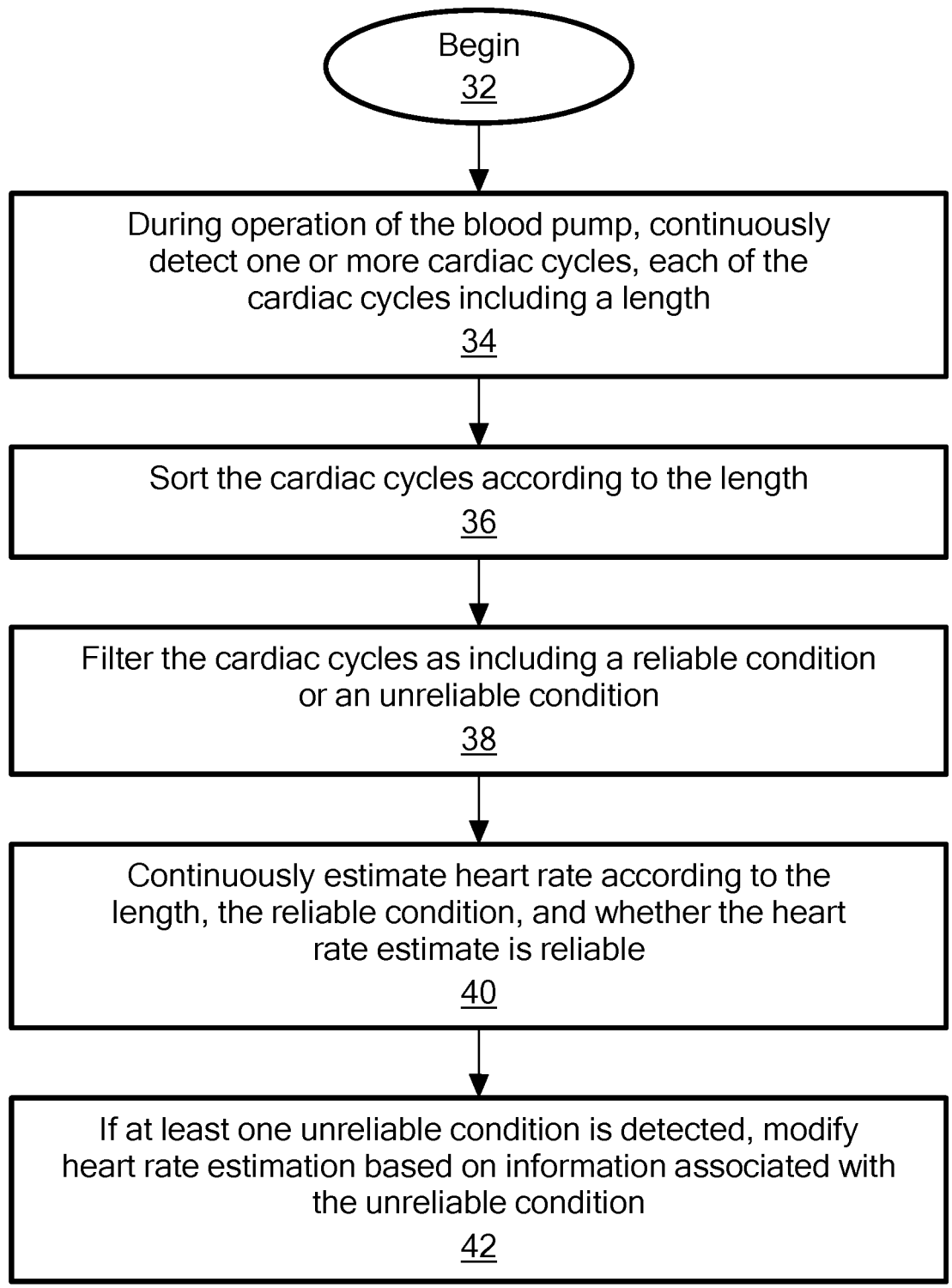
FIG. 2 is a flow diagram of a method of estimating a heart rate of a patient having the blood pump implanted in a body of the patient during operation of the blood pump.

FIG. 2 is a flow chart of a method 30 of estimating a heart rate of a patient having the implantable blood pump 12 during operation of the blood pump implanted in a body of the patient. For the purpose of heart rate diagnostics, the method 30 is configured to provide a real-time display of the heart rate on a monitor viewable by a physician, store heart rate diagnostics in log files with such diagnostics including, for example, a daily mean, a day versus night mean which may indicate heart failure status, rate histograms, and the like, and provide heart rate variability indications. The method 30 is described generally with respect to FIG. 2.

The method 30 includes process steps which may be stored in the memory 22 as the instructions 26 for execution by the processor 20, i.e., a heart rate algorithm. The process steps may be carried out in a different order and may include additional steps or exclude one or more of the steps provided. In one configuration, the method 30 begins at step 32 and proceeds to step 34 including, during operation of the blood pump, the processor 20 continuously detecting one or more cardiac cycles, each of the cardiac cycles including a length. At step 36, the method includes the processor 20 sorting the cardiac cycles according to the length. At step 38, the method includes filtering the cardiac cycles between those including a reliable condition and an unreliable condition. The unreliable condition may be a low pulsatility, at least one of the cardiac cycles including a length deviating from a standard length, a tachyarrhythmia, and/or an individual heart rate estimate considered unreliable using information from the cardiac cycles. The cardiac cycles including the length deviating from the standard length may also be described as including a series of cardiac cycles which have had highly variable cycle lengths, such that an estimate of the heart rate is no longer representative of physiological demand. Proceeding to step 40, the processor 20 continuously estimates a heart rate according to the length of the cardiac cycles and the reliable condition. Step 42 occurs simultaneously with respect to step 40. In step 42, if at least one unreliable condition is detected, the method includes modifying the heart rate estimation based on information associated with the unreliable condition that was detected. For example, modifying the heart rate includes excluding the unreliable condition from the heart rate estimation.

Figure 3:
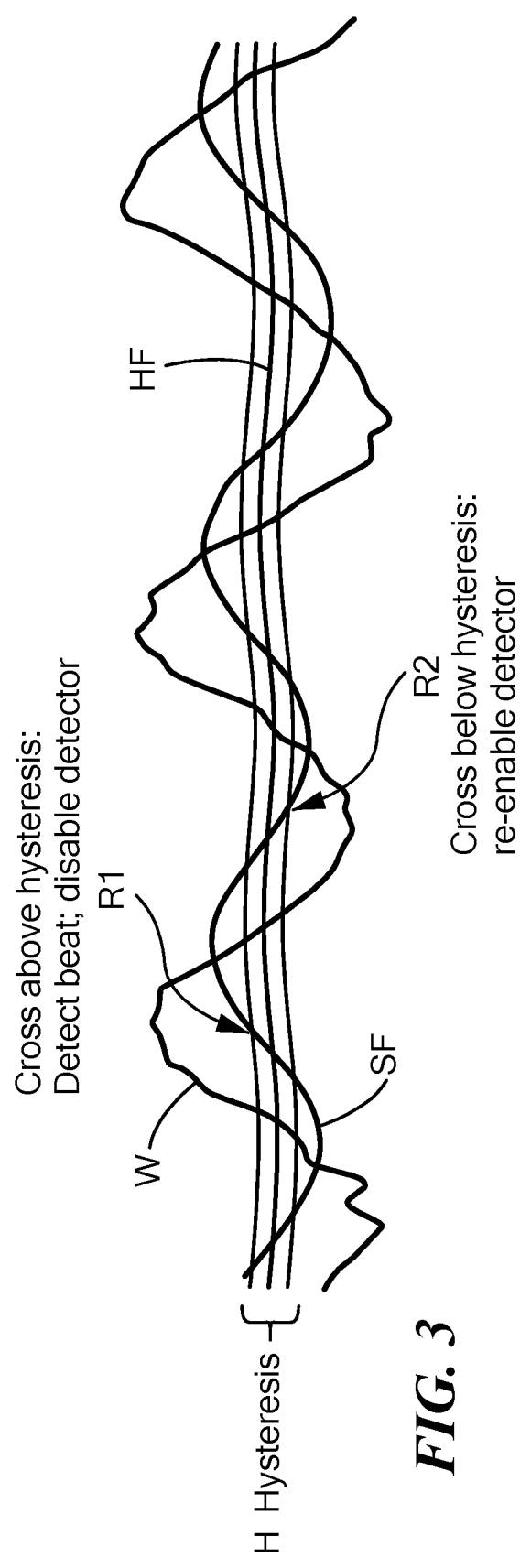
FIG. 3 is a graph of a raw current waveform passed through a soft lowpass filter and a hard lowpass filter to detect individual heartbeats in accordance with the method of FIG. 2.

FIG. 3 is a graph of an exemplary raw current waveform "W" passed through a soft lowpass filter and a hard lowpass filter to detect individual heartbeats. The soft lowpass filter smooths the current signal, which can contain high frequency noise, whereas the hard lowpass filter tracks baseline drift of the current waveform. A hysteresis "H", for example, of +/−4 mAmps, may be applied to the hard lowpass filter. The soft and hard filters may be determined through various methods, such as using difference equations having cutoff frequencies of between 1.95-2.0 Hz and 0.60-0.65 Hz, respectively, as examples.

A region "R1" indicates a heartbeat detected when a soft-filtered current signal "SF" rises above a hard-filtered current signal "HF" plus the added hysteresis offset. Subsequent heartbeat detection can occur after region "R2" when the soft filtered current signal passes below the hard-filtered current signal minus the hysteresis offset, as such event re-arms cardiac cycle detection. For example, the next beat is detected whenever the soft filtered current signal again rises above the hard-filtered current signal plus the hysteresis offset. The cardiac cycle length is determined by the time between neighboring heartbeats.

Figure 4:
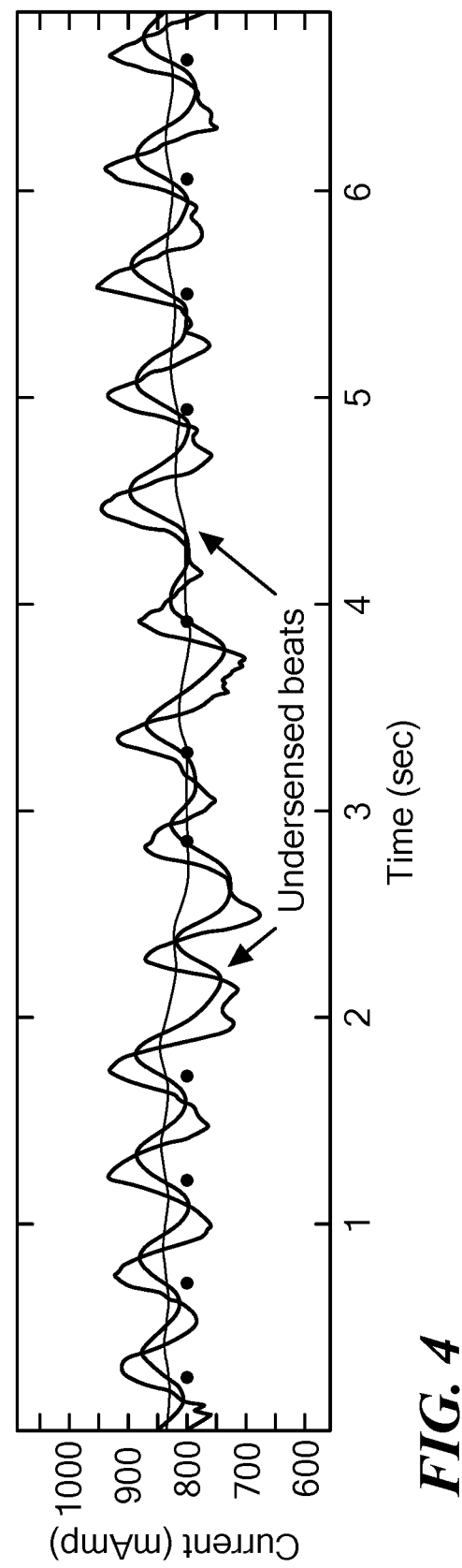
FIG. 4 is a graph depicting an example of cardiac cycle detection in accordance with the method of FIG. 2.

FIG. 4 is a graph depicting an example of cardiac cycle detection in accordance with step 34 including the current waveform W, the soft-filtered current signal SF, and the hard-filtered current signal HF plotted relative to current and time. The circles indicate the timing of each detected cardiac cycle and the arrows indicate two instances of under sensing, i.e., missed sensing of a cardiac cycle, which correspond to the unreliable condition or information.

FIG. 5 is a table listing cardiac cycles (in milliseconds) detected by the processor 20 executing the heart rate algorithm during operation of the blood pump 12 to continuously detect the most recent cardiac cycles of the patient, for example twelve cardiac cycles, to define a buffer "B". The length of the cardiac cycles is designated "L". Instances of under sensing "US" are indicated by cycle lengths that are multiples of the actual cycle length and oversensing "OS" is indicated by relatively small cycle lengths. The buffer is continuously updated using the length of each of the cardiac cycles in real time.

FIG. 6 is a table of the buffer of the cardiac cycles of FIG. 5 sorted from smallest to largest length. The heart rate algorithm selects an instantaneous heart rate estimate that is unbiased and is the least likely to be corrupted by an error in sensing by balancing under sensing and oversensing. For example, under sensing corrupts one entry in the buffer, starting from the right of the sorted buffer, whereas oversensing corrupts two entries in the buffer, starting from the left of the buffer. In an algorithm that produces rare errors in sensing with an approximate 3:1 ratio of under sensing to oversensing, the sixth entry in the buffer reflects a median heart rate estimate that is considered a relatively accurate heart rate estimate. As such, the heart rate estimates that are unreliable are excluded from the estimation.

Figure 7:
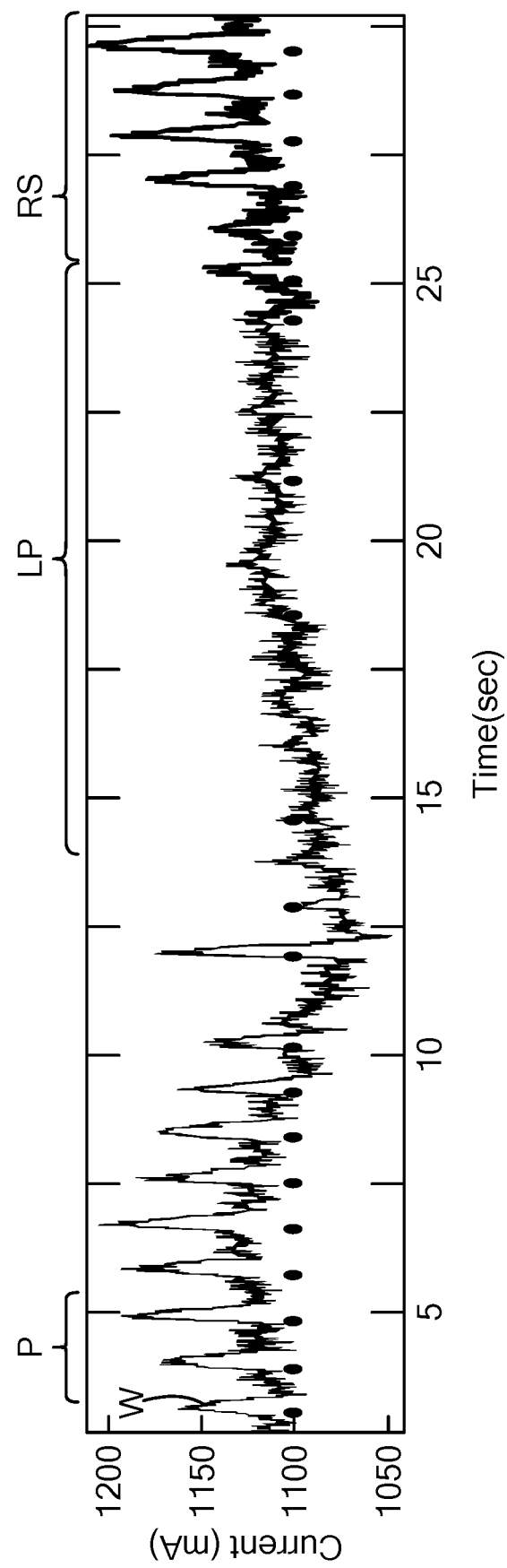
FIG. 7 is a graph depicting a current waveform including peak-to-peak deflection associated with the cardiac cycles representing pulsatility.

FIG. 7 is a graph depicting the current waveform "W" including peak-to-peak deflection associated with the cardiac cycles, referred to as pulsatility, which provides an indication of contractility of the native heart. The circular dots represent heartbeats. When the contractility is weak or when preload is minimal, the peak-to-peak deflection of the current signal may be inadequate to produce reliable sensing of the cardiac cycles. To avoid corruption of the heart rate estimation, the pulsatility is estimated and the inadequate signals are excluded from the heart rate estimation. For example, FIG. 7 depicts the pulsatility "P" being calculated over a two second moving window, wherein the pulsatility is the difference between the maximum and the minimum current in the two second window. If the pulsatility falls below a predetermined threshold, the pulsatility is considered to be inadequate to produce reliable sensing of cardiac cycles and thus unreliable, triggering the automatic exclusion of the associated cardiac cycles from the heart rate estimation. In the alternative, the result of the heart rate estimate may be selectively ignored when unreliable, i.e., in the presence of the unreliable condition. FIG. 7 depicts a low pulsatility duration "LP" during which time there is no reported heart rate for the heart rate estimation.

In one example, the predetermined pulsatility threshold for indicating low pulsatility may be between 45-50 mAmps and may trigger a low pulsatility alert which continues until the pulsatility meets or exceeds a second predetermined threshold, for example 70 mAmps. The low pulsatility alert is cleared when the pulsatility exceeds the second predetermined threshold. The buffer of cardiac cycles may be reset when the duration of the low pulsatility alert continues for a predetermined duration, for example, after ten to fifteen consecutive seconds of unreliable cardiac cycles, and the low pulsatility alert is cleared. FIG. 7 depicts a region "RS". At the start of this region, the buffer of cardiac cycles is cleared. New cardiac cycles that are obtained after the low pulsatility alert has cleared are again added to the buffer.

Figure 8:
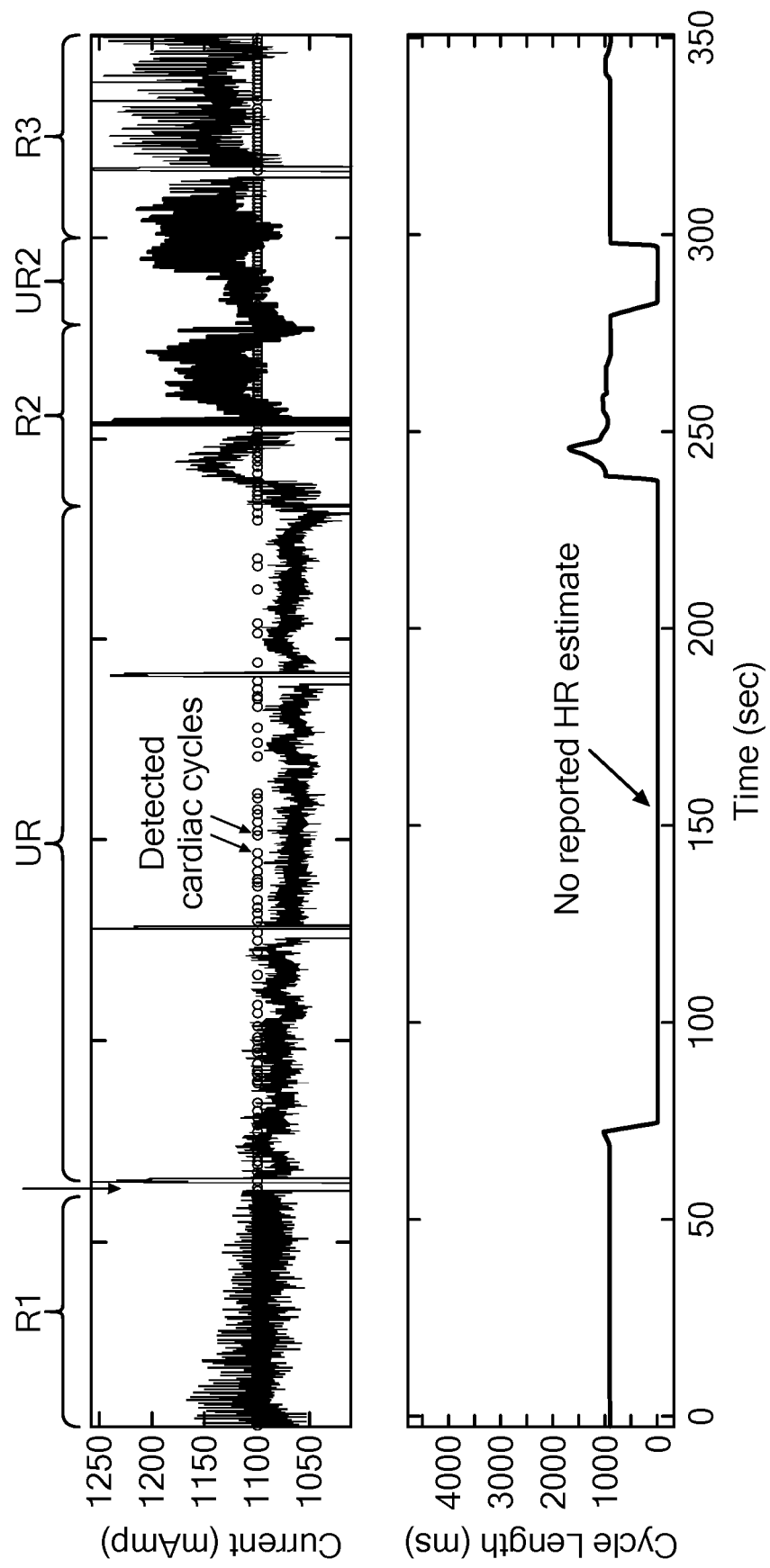
FIG. 8 is two graphs, wherein the top graph is an expanded view of the graph of FIG. 7 and the bottom graph is the resulting heart rate estimate provided using the information of the top graph and FIG. 7.

FIG. 8 depicts two graphs, wherein the top graph is an expanded view of the graph of FIG. 7 including a first reliable pulsatility region "R1", an unreliable pulsatility region "UR", a second reliable pulsatility region "R2", a second unreliable pulsatility region "UR2", and a third reliable pulsatility region "R3". The bottom graph is the resulting heart rate estimation provided using the information of the top graph and FIG. 7. The line marked "HR" is the proposed heart rate estimation from the exemplary report. Periods of unreliable heart rate are indicated by the arbitrary value of "0" in the cycle length of the line HR.

As stated above, another type of unreliable condition which is excluded from heart rate estimation includes a number of the cardiac cycles being highly variable with respect to other cardiac cycles. In order to determine the cardiac cycles classified as being highly variable, the algorithm defines a running average of the absolute beat-to-beat differences in a pair of adjacent cardiac cycles and the running average is compared to a predetermined threshold, which is normalized by the average cycle length. The running average being greater than a predetermined threshold percentage of the average cycle length indicates a period of highly variable cardiac cycles, and the highly variable cardiac cycles are excluded from the heart rate estimation. In addition, during the highly variable cardiac cycles, a closed-loop control algorithm associated with controlling the blood pump 10 may switch from a heart rate-based control to the secondary source of information, i.e., an alternate method of estimating physiologic demand. The highly variable cardiac cycle lengths may be indicative of atrial fibrillation, ventricular fibrillation, or a high prevalence of ectopy, such as bigeminy, trigeminy, etc. Highly variable cardiac cycle lengths could also occur from unreliable sensing. The threshold percentage of the average cycle length may be, for example, approximately 21%. To clear the highly-variable cardiac cycle length condition, the running average must then pass below a lower threshold, such as approximately 17%. The term approximately includes a deviation between plus or minus 2-3%. Such percentages are provided as exemplary and are not intended to be limiting.

The following example with respect to the highly variable cardiac cycles is provided for illustrative purposes and is not intended to be limiting. The running average of the absolute beat-to-beat differences in adjacent cycle lengths may be called a MeanVar and may be initialized to 50 ms. The average cycle length may be called a RRmean. The absolute difference between each consecutive pair of cardiac cycles is AbsDiff and is first constrained, so that no single entry dominates the running average. Accordingly, if AbsDiff−MeanVar>max(MeanVar, 20 ms), then AbsDiff=MeanVar+max(MeanVar, 20 ms). When no tachyarrhythmia has been detected, as explained below, the MeanVar is updated according to MeanVar[n]=0.9625*MeanVar[n−1]+0.0375*AbsDiff. During detected tachyarrhythmias, the value of MeanVar is frozen. A different equation is applied to update MeanVar during a reset mode as MeanVar[n]=0.5*MeanVar[n−1]+0.5*AbsDiff. Finally, MeanVar is constrained to be no larger than 0.25*RRmean and no smaller than 10 ms.

The periods of the high variability of cardiac cycles may be instantaneously displayed on a monitor, such as the interface 24 of the controller 14. During the duration of the highly variable cardiac cycles, the algorithm continues to sense cardiac cycles, the buffer of the most recent cardiac cycles continues to be filled, and a tachyarrhythmia detection system remains active.

As referenced above, tachyarrhythmia, not including sinus tachycardia, is an unreliable condition for the purpose of approximating physiological demand, i.e., considered to include unreliable information. During a tachyarrhythmia, a heart rate estimate may be reliable, i.e., accurate, but for the purpose of controlling a pump, tachyarrhythmia is an unreliable estimate of physiologic demand. Tachyarrhythmias are indicated by a relatively sudden, non-physiologic increase in heart rate relative to a standard or smooth heart rate. Tachyarrhythmia detection may be governed by one or more programmable thresholds stored in the memory 22 of the controller 14. For the purpose of performing diagnostics, the tachyarrhythmia is detected when the tachyarrhythmia criteria (described below) are met continuously for a pre-defined duration threshold, and the heart rate exceeds a heart rate threshold at least once during this duration. For example, the heart rate threshold may be between 150 to 200 BPM and the duration may be the tachyarrhythmia lasting for at least 20 to 60 seconds. Another programmable threshold is a sinus tachycardia limit "ST Limit". Heart rates above this threshold will be considered tachyarrhythmias whether or not the tachyarrhythmia criteria (described below) are met as these rates are too fast to be sinus tachycardia.

The processor 20 may be configured to perform a diagnostic function based on the tachyarrhythmia. The diagnostic function may be, for example, an alert, i.e., an auditory or visual alert emitted through a speaker (not shown) or the interface 24 of the controller 14 or the alert may be transmitted to a remote location, such as a physician's office. In another example, the diagnostic function is a recommended or automatic change in pump parameter, such as a recommended increase in pump flow.

In one example, a tachyarrhythmia is detected by applying the algorithm to establish and maintain an adaptive "R-R expected range" which consists of the mean the +/− the variability of the most recent trend of cardiac cycles "R-R intervals" (RRmean±RRmad) such that the next cardiac cycle is expected to lie within the RRmean±RRmad, where mad=mean absolute difference, a metric of variability. Cardiac cycles that are consistently shorter than RRmean−RRmad are an indication of sudden rate acceleration or tachyarrhythmia. Tachyarrhythmia detection occurs when a counter of consecutive R-R intervals that are shorter than the expected range exceeds a predefined threshold (for example, seven beats).

During normal operation, each new R-R interval, in ms, that is greater than or equal to an ST Limit, in ms, is compared to the expected range, i.e., RRmean±RRmad, that was established after processing the prior R-R interval. If the new R-R interval is within the expected range, the current R-R interval is classified as expected; otherwise, the current R-R interval is classified as unexpected. The classification of expected or unexpected determines if the R-R interval contributes to tachyarrhythmia detection, as explained below, and determines if the R-R interval is acceptable for use in updating the RRmean and RRmad. For expected R-R intervals, a new RRmad is computed by:

$$RRmad = 0.95 \times RRmad +$$
$$0.05 \times 7/3 \times (|RR - RRmean| + 0.02875 * RRmean) \times \left(1 - \frac{750 - RRmean}{1000}\right)$$

Where RR is the new R-R interval; RR, RRmad and RRmean are in milliseconds; || represents absolute value; |RR−RRmean| is the absolute difference that is the primary input to the calculation of RRmad, 7/3 is a factor to stabilize the expected range (because values outside of the expected range are excluded from the adaptation process); the added 0.02875*RRmean places a constraint on the minimum size of RRmad; and the factor $$\left(1 - \frac{750 - RRmean}{1000}\right)$$

forces the expected range to tighten as the heart rate increases and to expand as the heart rate decreases. If the algorithm is not in Reset mode (as explained below), additional constraints are then placed on the size of RRmad, such as the maximum allowed RRmad is 0.2188×RRmean and the minimum allowed RRmad is 15 ms. For expected R-R intervals, a new RRmean is computed by: RRmean=0.9× RRmean+0.1×RR. The coefficients 0.95 and 0.05 in the RRmad equation and 0.9 and 0.1 in the RRmean equation are complimentary adaptation factors that determine the rate of adaptation of the algorithm. These coefficients are modified temporarily in the reset mode, as described below. Further, R-R intervals that are classified as unexpected do not contribute to updating RRmad and RRmean. R-R intervals that are below the ST Limit are classified as unexpected, and they do not influence a lost counter or a reset counter, as explained below.

The algorithm begins in a reset mode, where the RRmean is initialized to a time, such as 900 ms, and the RRmad is initialized to a time, such as 800 ms, and the first five R-R intervals, which may be handled by setting a reset counter to five. After each adaptation step of RRmean and RRmad, the reset counter is decremented. When in the reset mode, the adaptation factors for RRmean and RRmad are set to 0.5. In reset mode, if the current R-R interval is not expected or if the current R-R interval is less than a predetermined detection rate (for example, 100 to 120 BPM), the expected range is not updated and that beat does not decrement the reset counter. When the reset counter is decremented to zero, the adaptation factors return to a designated value for the RRmad and the RRmean. The same reset mode behavior occurs when a duration of low pulsatility has been observed, for example for at least ten consecutive seconds of low pulsatility.

The system 10 may include a lost feature configured to prevent the expected range from getting lost as the expected range does not adapt when the R-R intervals fall outside of the expected range. Thus, the algorithm tracks of the number of beats with R-R intervals that are consistently outside of the expected range using a lost counter. Unexpectedly long R-R intervals are indicated by the current R-R interval being greater than RRmean+RRmad, whereas unexpectedly smaller R-R intervals are indicated by the current R-R interval being less than RRmean−RRmad. A value of the lost counter is incremented or decremented based on the comparison. For example, when the current R-R interval is greater than RRmean+RRmad, the lost counter is incremented. If the lost counter reaches a threshold value (for example twelve), the RRmean may be adjusted toward a larger value so that the expected range recaptures the recent trend of R-R intervals.

Figure 9:
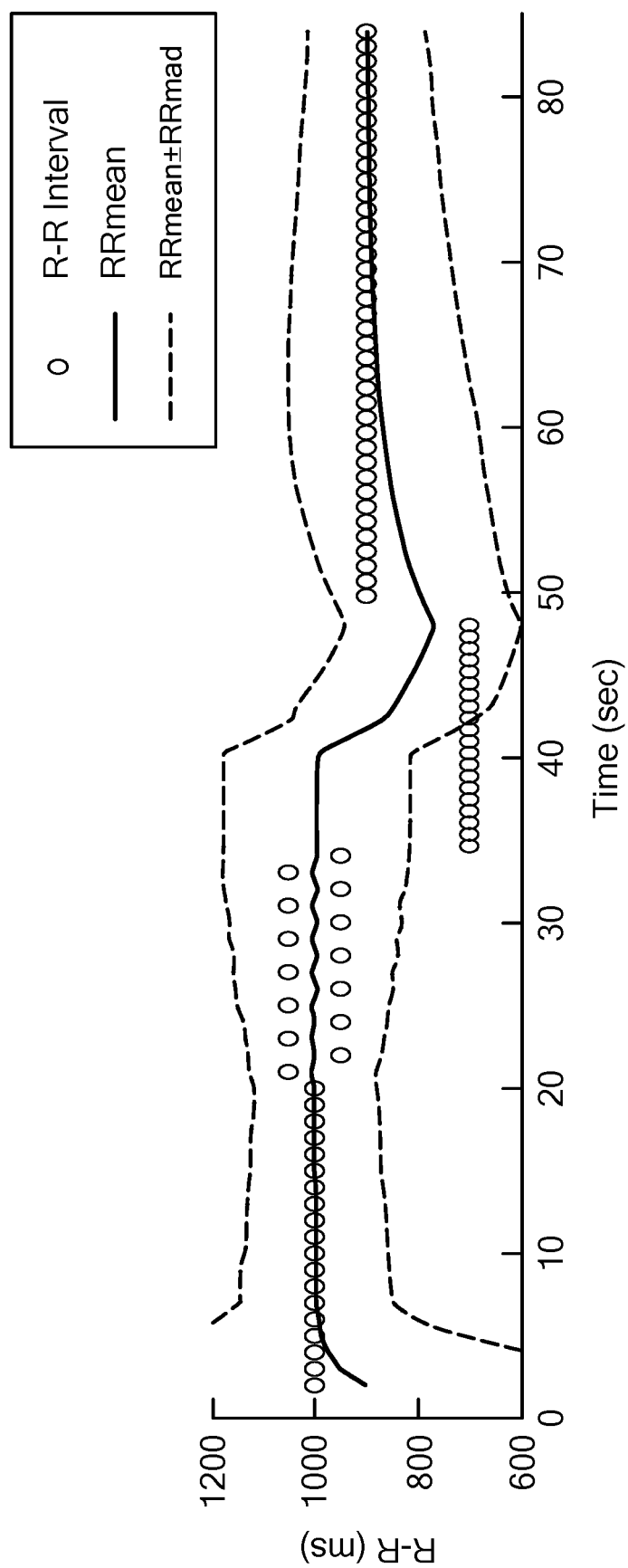
FIG. 9 is a graph showing an example of the behavior of an R-R expected range.

FIG. 9 is a graph depicting the behavior of the R-R expected range. The reset mode completes in the first five R-R intervals. Thereafter, in the example depicted in FIG. 9, the expected range (RRmean±RRmad) slowly tightens around a string of consistent 1000 ms R-R intervals. Next, variability in the R-R intervals causes the expected range to expand. At approximately 34 seconds, the R-R intervals rapidly decrease, but are still greater than the detection rate which is set to 500 ms. Initially, adaptation halts as the R-R intervals are consistently unexpected. After 12 consistently unexpected short R-R intervals, the criteria for the lost feature are met. The expected range is then shifted toward smaller values until the 700 ms R-R intervals fall within the expected range, at approximately 42 seconds. Thereafter, criteria for lost mode are no longer met and normal adaptation occurs. Finally, the R-R intervals suddenly increase to 900 ms and because the R-R intervals are within the current expected range, normal adaptation occurs, and the expected range eventually tightens around 900 ms.

Figure 10:
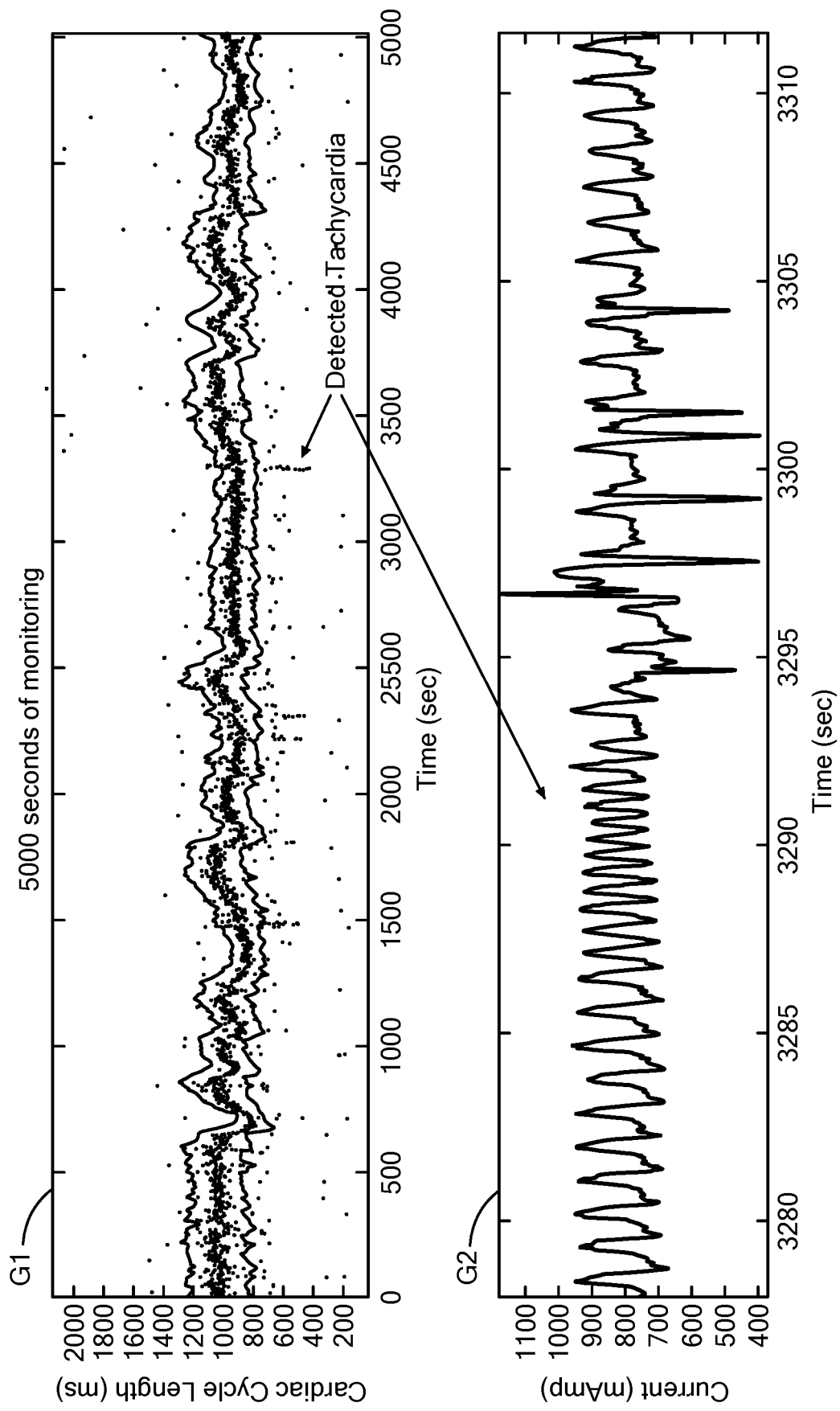
FIG. 10 is two graphs showing an example of tachyarrhythmia detection.

FIG. 10 depicts two graphs showing an example of tachyarrhythmia detection including the graph "G1" showing a detection rate set to 600 ms and a detection duration threshold set to seven beats. The individual cardiac cycles are indicated by circular dots and the R-R expected range is indicated by the solid lines. The graph "G2" depicts a raw HVAD current waveform showing that the tachyarrhythmia was appropriately detected. In sum, for the purpose of tachyarrhythmia diagnostics, tachyarrhythmia detection occurs when a tachyarrhythmia has been detected according to the criteria above, the duration of the tachyarrhythmia between the point of initial detection and a point of termination is at least the detection duration threshold, and at least once during the duration of the tachyarrhythmia, the heart rate estimate, i.e., obtained from the buffer, was greater than the detection rate threshold. Periods of low pulsatility that occur during a detected tachyarrhythmia will count toward the duration of the tachyarrhythmia.

Following a tachyarrhythmia detection, the algorithm switches from maintaining the expected range to searching for tachyarrhythmia termination criteria. There are two criteria for tachyarrhythmia termination, the first being the most recent cardiac cycles being consistently back within the expected range and the second being the most recent cardiac cycles being equal to or exceeding the detection rate threshold. The algorithm maintains two separate counters which keep track of the evidence for termination according to each of the two criteria. When either of the counters exceeds a threshold (for example, five), tachyarrhythmia termination is declared and the algorithm returns to normal operation of adjusting the expected range with each new detected beat.

The system 10 may be configured to store, in the memory 22, episodes of tachyarrhythmia detection of special interest as may be determined by a clinician, including raw blood pump waveforms before, during, and after the tachyarrhythmia. The system 10 may set an alarm, alert, or the like, and/or activate a contact to a physician in the event of a high-risk tachyarrhythmia, such as one that is relatively fast for the patient's typical state. Further, when in a detected tachyarrhythmia, the patient's native heart function may be decreasing such that a pump parameter should be adjusted, such as increasing the pump flow to compensate for the decrease in native heart function.

Figure 11:
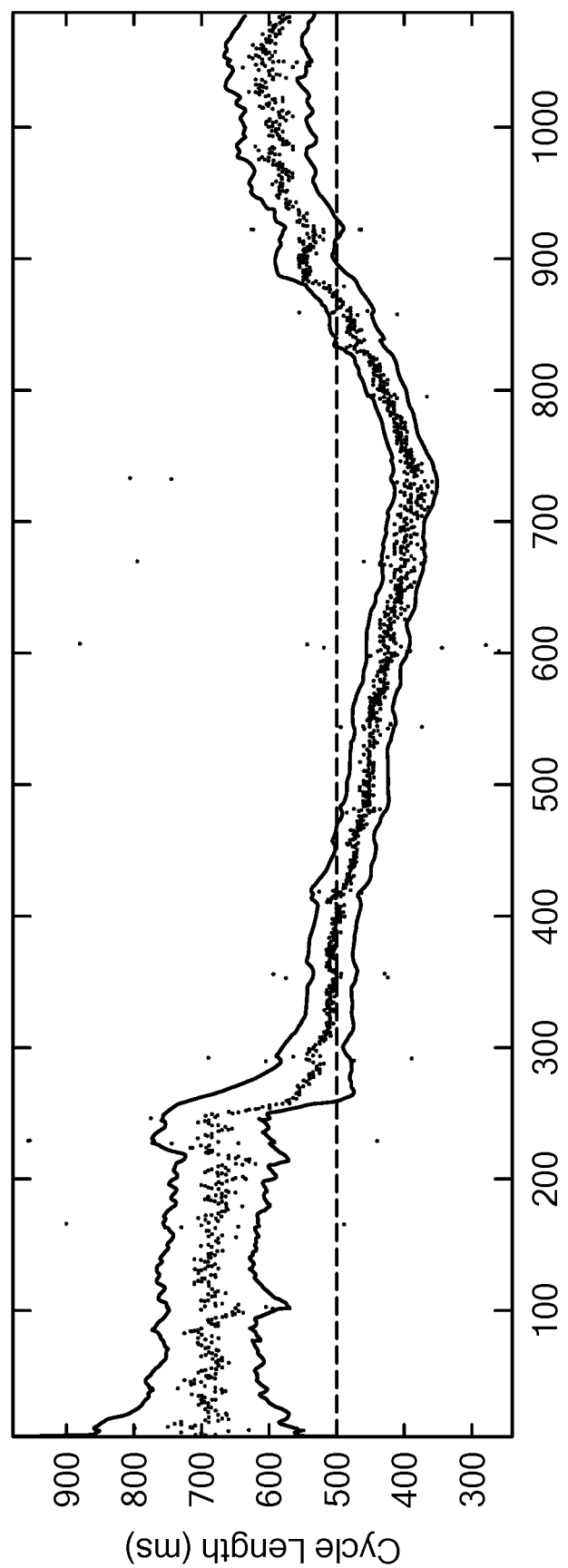
FIG. 11 is a graph depicting heart rate results from a current waveform of the blood pump collected during exercise.

The method 30 of estimating the heart rate can serve as the primary estimator of physiologic demand for a closed-loop controller. For a given heart rate, the controller, such as the controller 14, will aspire to achieve a desired flow setting, subject to determination of sufficient preload and absence of suction. FIG. 11 is a graph depicting heart rate results from the current waveform of the blood pump collected during exercise. The circles indicate the individual cardiac cycle lengths, whereas the lines around the circles indicate the R-R expected range which tracks the smooth acceleration and deceleration of heart rate. Because the heart rate remains within the expected range, it may be appropriately used to estimate physiologic demand and control pump speed. The desired pump flow could, for example, have a linear relationship to estimated heart rate. The actual pump flow may be constrained to be less than the desired flow because of suction detection, inadequate preload, or a high-power constraint.

The closed-loop control of pump function will not rely on the heart rate estimate whenever the heart rate estimate includes the unreliable condition or information. As discussed above, the unreliable condition is at least one of the low pulsatility, the highly variable cycle lengths, or the tachyarrhythmia. During the unreliable heart rate estimate, the closed-loop algorithm may translate from the closed-loop control to an alternate method of controlling the blood pump based on a secondary source of information indicating physiological demand, such as an activity-based estimate of physiological demand or open-loop pumping. The activity-based estimate may include the use of a sensor, such as activity counts and/or an accelerometer, to obtain information associated with physiological demand.

For the purpose of inhibiting the closed-loop pump control method as it relates to a tachyarrhythmia, a second detection rate threshold and a second detection duration threshold may be used which are lower than the values designated for diagnostic purposes discussed above. For example, the detection rate threshold includes detecting when the heart rate exceeds a heart rate threshold and the detection duration threshold includes detecting a duration of the tachyarrhythmia exceeding a duration threshold including the tachyarrhythmia being sustained for at least this number of cardiac cycles. Based on the tachyarrhythmia exceeding the heart rate threshold and the duration threshold, the processor 20 causes the system 10 to automatically switch from the closed loop control method to the alternate heart rate estimation method. The heart rate threshold may vary and is between 80 to 150 BPM in one example.

Figure 12:
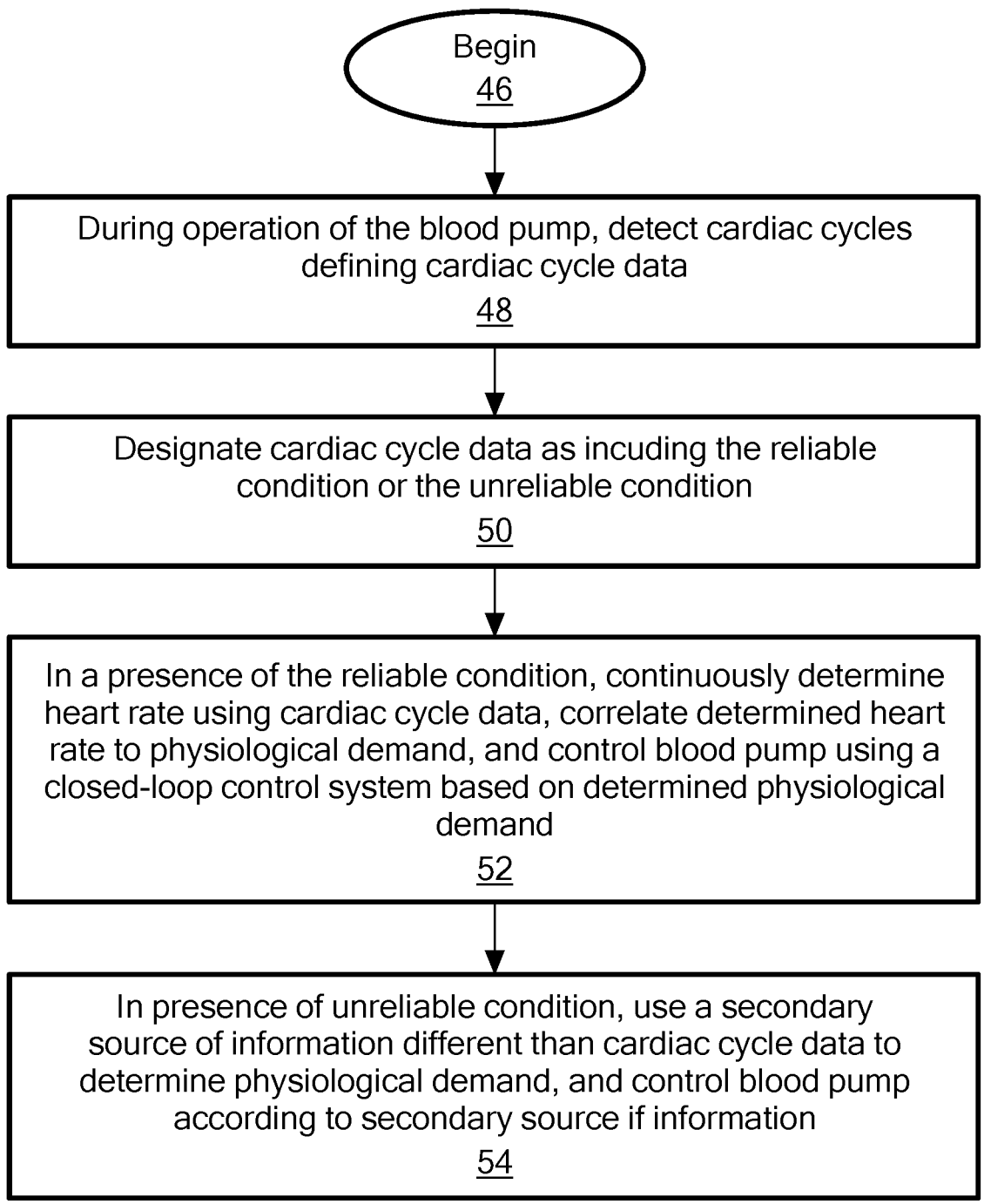
FIG. 12 is a flow diagram of a method of controlling an implantable blood pump.

Referring to FIG. 12, a method 44 of controlling the blood pump 12 using the closed loop control method and/or the secondary source of information representing the physiological demand is provided, as discussed above. The process steps may be carried out in a different order and may include additional steps or exclude one or more of the steps provided. In one configuration, the method 44 begins at step 46 and proceeds to step 48 including, during operation of the blood pump 12, detecting the cardiac cycles defining cardiac cycle data, such as using the processor 20. At step 50, the method includes designating the cardiac cycle data as including the reliable condition or the unreliable condition.

At step 52, in a presence of the reliable condition, the method includes continuously determining the heart rate using the cardiac cycle data, correlating the determined heart rate to the physiological demand, and controlling the blood pump using the closed-loop control system based on the determined physiological demand. At step 54, in a presence of the unreliable condition, the method includes using the secondary source of information different than the cardiac cycle data to determine the physiological demand, and control the blood pump according to the secondary source of information.

Figure 13:
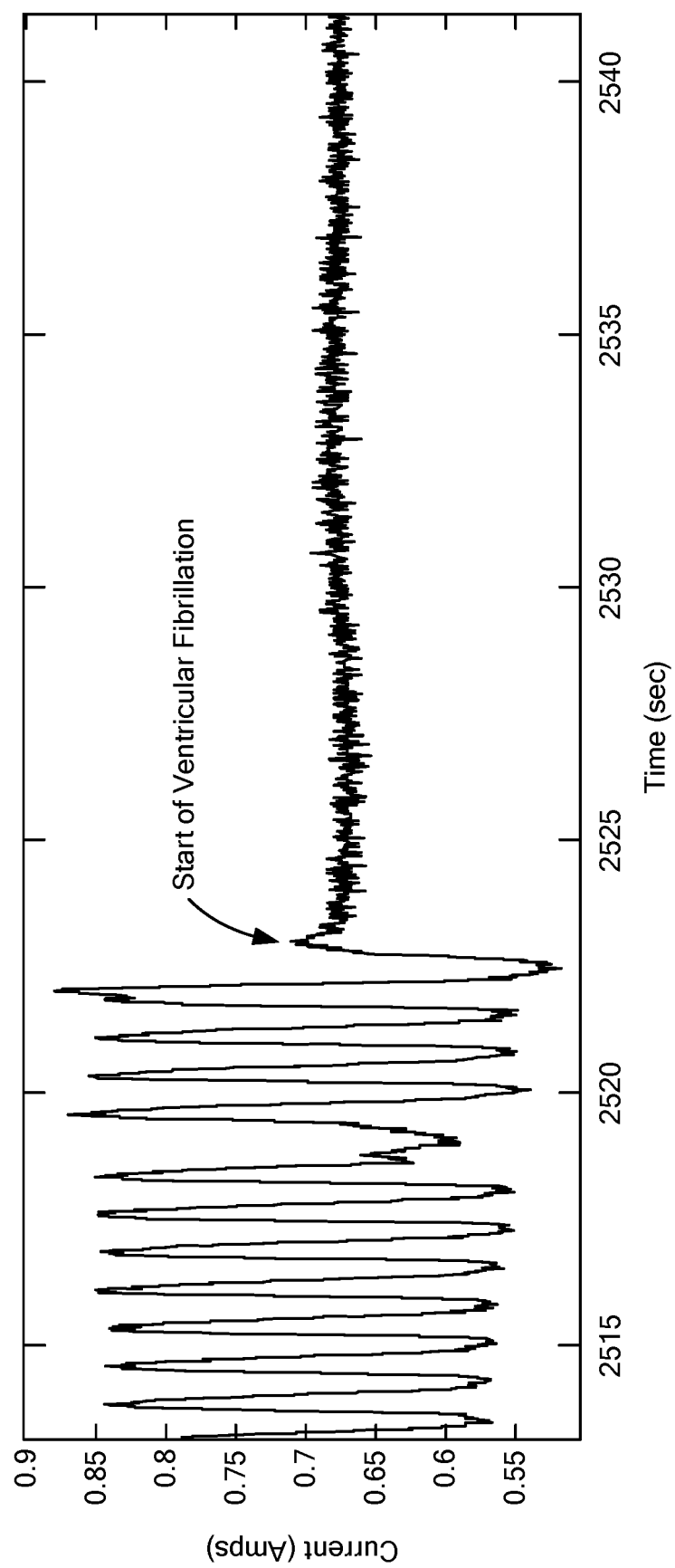
FIG. 13 is a graph showing current as a function of time and showing ventricular fibrillation and the associated drop in pulsatility.
Figure 14:
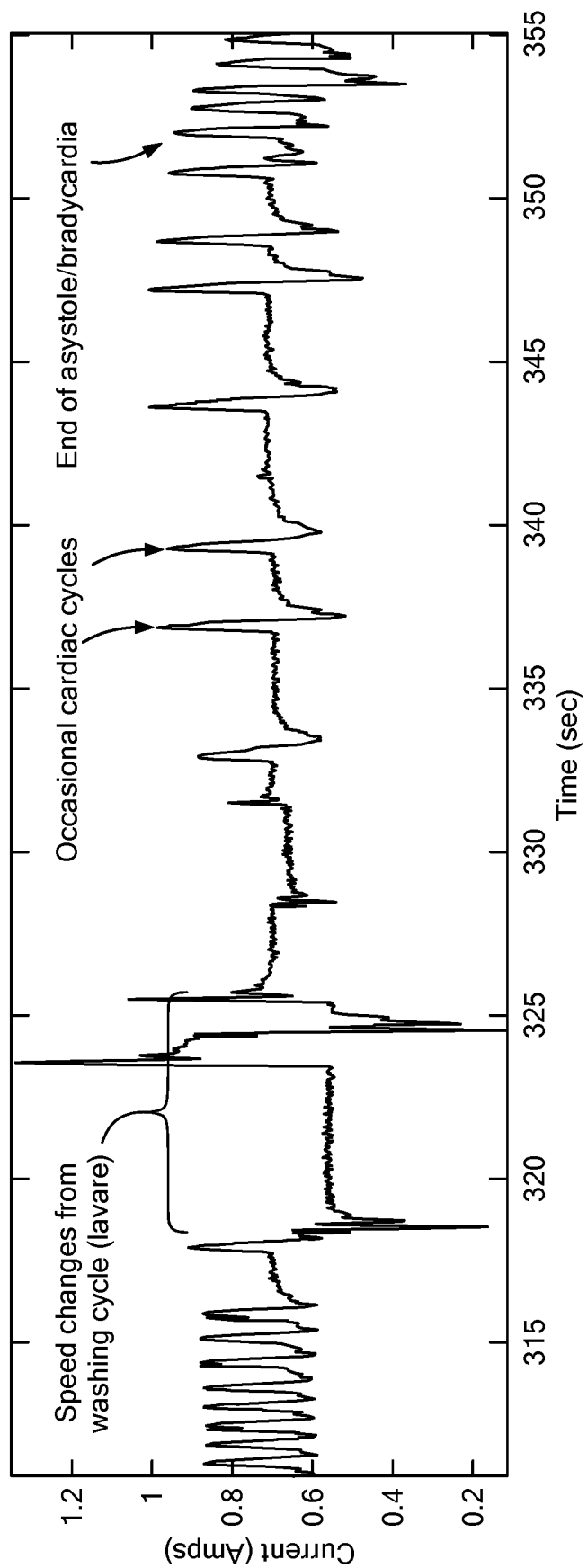
FIG. 14 is a graph showing current as a function and showing a decrease in pulsatility with asystole or extreme bradycardia.
Figure 15:
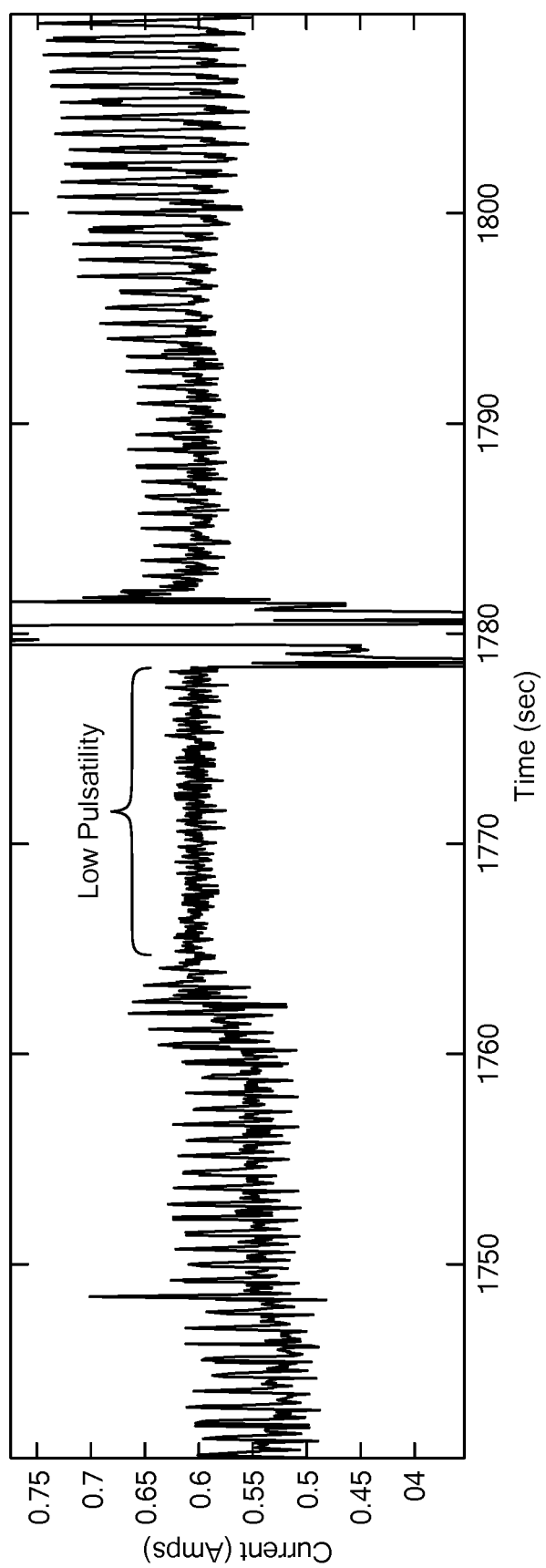
FIG. 15 is a graph showing current as a function and showing a slower drop in pulsatility as a result of decreased preload or contractility of the heart.

Referring now to FIGS. 13-15, in another embodiment, detection of low pulsatility or highly variable cardiac cycle lengths may result in the pump speed transitioning to a pre-programmed resting speed. Reduction of pump speed to the resting speed may also be advantageous following detection of low pulsatility, because low pulsatility may be a sign of impending suction, and reduction of speed to the resting speed may help avoid the development of suction. During tachyarrhythmia or other adverse cardiac events, however, the pump speed may be held constant at the speed set according to the last known reliable heart rate estimate. Thus, if the heart rate was elevated prior to the onset of the tachyarrhythmia, the corresponding elevated pump speed would be maintained during the extent of the tachyarrhythmia, which may be advantageous for the patient compared to setting the pump to resting speed when the tachyarrhythmia is detected.

Moreover, in another method of detecting an unreliable condition, if the current 2-second period has a low value of the maximum-minus-minimum current (also known as pulsatility), for example, pulsatility less than 45 mAmps, the algorithm looks at the pulsatility of prior 2-sec segments. If the pulsatility for the period 0-2 seconds prior to the current 2-second period is significantly greater (for example, greater than 125 mAmps) or if the pulsatility for the period 2-4 seconds prior to the current 2-second period is significantly greater (for example, greater than 125 mAmps), a sudden drop in pulsatility is detected, which is indicative of asystole, extreme bradycardia, ventricular fibrillation, or other adverse cardiac events. FIG. 13 shows the sudden drop in pulsatility when ventricular fibrillation begins. FIG. 14 shows a similar rapid decrease in pulsatility with asystole or extreme bradycardia. The asystole/bradycardia begins at 316 seconds and ends at 351 seconds. Occasional cardiac cycles are seen during this time. FIG. 15 shows a slower drop in pulsatility as a result of decreased preload or contractility of the heart. This may indicate a pre-suction condition and the best course of action is to decrease pump speed to the pre-programmed resting speed. Detection of asystole, extreme bradycardia, or ventricular fibrillation in this manner may be useful for diagnostic purposes and for control of pump speed. For diagnostics, this could result in storage of a waveform or generation of an alarm or other indication that asystole, extreme bradycardia, or ventricular fibrillation is present. For closed-loop control of pump speed, asystole, extreme bradycardia, or ventricular fibrillation may result in maintaining pump speed at the speed set according to the most recent reliable heart rate (i.e., the same treatment as tachyarrhythmias). This is distinct from the other reasons for low pulsatility, which result in pump speed being set to resting speed.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of estimating a heart rate of a patient having an implantable blood pump comprising:
   during operation of the blood pump:
      continuously detecting a plurality of cardiac cycles, each of the plurality of cardiac cycles including a length;
      sorting the plurality of cardiac cycles according to the length;
      filtering the plurality of cardiac cycles between one of a group consisting of including a reliable condition and at least one unreliable condition;
      continuously estimating a heart rate according to the length of the plurality of cardiac cycles and the reliable condition;
      calculating a pulsatility of the estimated heart rate over a predetermined time interval;
      comparing the calculated pulsatility to a predetermined threshold;
      determining whether the at least one condition includes low pulsatility based on the comparison of the calculated pulsatility and the predetermined threshold; and
      if the at least one unreliable condition is detected, modifying the estimated heart rate based on the detected at least one unreliable condition.

2. The method of claim 1, wherein the at least one unreliable condition includes an individual heart rate estimate.

3. The method of claim 1, wherein the unreliable condition further includes one selected from the group consisting of the plurality of cardiac cycles including a length deviating from a standard length, and a tachyarrhythmia.

4. The method of claim 3, further comprising generating a low pulsatility alert when the unreliable condition is the low pulsatility, and, during a duration of the low pulsatility alert, automatically excluding the plurality of cardiac cycles from the heart rate estimating.

5. The method of claim 4, wherein the plurality of cardiac cycles define a buffer, and the buffer is reset when the duration of the low pulsatility alert continues for a predetermined duration.

6. The method of claim 1, further comprising:
   defining a running average of a beat-to-beat difference in a pair of adjacent cardiac cycles of the plurality of cardiac cycles; and
   classifying at least one of the plurality of cardiac cycles as including the unreliable condition when the running average is greater than a predetermined percentage of a predetermined average.

7. The method of claim 1, further comprising detecting and maintaining an R-R expected range.

8. The method of claim 1, wherein the plurality of cardiac cycles define a buffer, and the buffer is continuously maintained using a most recent plurality of cardiac cycles.

9. A system of estimating a heart rate of a patient comprising:
   an implantable blood pump;
   a controller in communication with the implantable blood pump and including a processor, the processor being configured to:
      during operation of the blood pump:
         continuously detect a plurality of cardiac cycles, each of the plurality of cardiac cycles including a length;
         sort the plurality of cardiac cycles according to the length;
         filter the plurality of cardiac cycles between one of a group consisting of including a reliable condition and at least one unreliable condition;
         continuously estimate a heart rate according to the length of the plurality of cardiac cycles and the reliable condition;
         calculating a pulsatility of the estimated heart rate over a predetermined time interval;
         comparing the calculated pulsatility to a predetermined threshold;
         determining whether the at least one condition includes low pulsatility based on the comparison of the calculated pulsatility and the predetermined threshold; and
         if the at least one unreliable condition is detected, modify the estimated heart rate based on information associated with the detected at least one unreliable condition.

* * * * *